US010349986B2

(12) United States Patent
Wall et al.

(10) Patent No.: US 10,349,986 B2
(45) Date of Patent: Jul. 16, 2019

(54) SPINAL IMPLANT SYSTEM AND METHOD

(71) Applicant: Warsaw Orthopedic, Inc., Warsaw, IN (US)

(72) Inventors: Daniel Paxton Wall, Cordova, TN (US); Richard Quinn Brown, Collierville, TN (US); Adam Glaser, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 57 days.

(21) Appl. No.: 15/492,867

(22) Filed: Apr. 20, 2017

(65) Prior Publication Data

US 2018/0303522 A1 Oct. 25, 2018

(51) Int. Cl.

| | |
|---|---|
| ***A61B 17/70*** | (2006.01) |
| ***A61B 34/20*** | (2016.01) |
| ***A61B 34/30*** | (2016.01) |
| ***A61B 17/88*** | (2006.01) |

(52) U.S. Cl.

CPC ...... *A61B 17/7082* (2013.01); *A61B 17/8875* (2013.01); *A61B 34/20* (2016.02); *A61B 34/30* (2016.02)

(58) Field of Classification Search

CPC ............ A61B 17/7076; A61B 17/7077; A61B 17/7079; A61B 17/708; A61B 17/7082; A61B 17/7083; A61B 17/7085; A61B 17/7086; A61B 17/7091

USPC ........................... 606/86 A, 96, 99, 102, 104

See application file for complete search history.

(56) References Cited

U.S. PATENT DOCUMENTS

| | | | |
|---|---|---|---|
| 6,285,902 | B1 | 9/2001 | Kienzile et al. |
| 6,301,495 | B1 | 10/2001 | Gueziec et al. |
| 6,322,567 | B1 | 11/2001 | Mittelstadt et al. |
| 6,441,577 | B2 | 8/2002 | Blumenkranz et al. |
| 6,527,443 | B1 | 3/2003 | Vilsmeier |
| 6,674,916 | B1 | 1/2004 | Deman et al. |
| 7,142,633 | B2 | 11/2006 | Elberhard et al. |
| 7,169,141 | B2 | 1/2007 | Brock et al. |
| 7,194,120 | B2 | 3/2007 | Wicker et al. |
| 7,235,076 | B2 | 6/2007 | Pacheco |
| 7,623,902 | B2 | 11/2009 | Pacheco |
| 7,776,048 | B2 | 8/2010 | Neubauer et al. |
| 7,776,065 | B2 | 8/2010 | Griffiths et al. |
| 7,903,851 | B2 | 3/2011 | Reisman et al. |
| 7,954,682 | B2 | 3/2011 | Reisman et al. |
| 7,957,831 | B2 | 6/2011 | Isaac |
| 8,014,575 | B2 | 9/2011 | Weiss et al. |
| 8,052,688 | B2 | 11/2011 | Wolf, II |
| 8,121,370 | B2 | 2/2012 | Dewaele |
| 8,121,371 | B2 | 2/2012 | Dewaele |
| 8,146,874 | B2 | 4/2012 | Yu |
| 8,175,349 | B2 | 5/2012 | Jerebko et al. |
| 8,218,843 | B2 | 7/2012 | Edlauer et al. |
| 8,219,177 | B2 | 7/2012 | Smith et al. |
| 8,219,178 | B2 | 7/2012 | Smith et al. |
| 8,277,461 | B2 | 10/2012 | Pacheco |

(Continued)

*Primary Examiner* — Julianna N Harvey
*Assistant Examiner* — Christina NegrelliRodriguez

(57) ABSTRACT

A surgical instrument comprises a first member including a drive engageable with a first mating surface of a bone fastener. A second member is rotatable relative to the first member and includes an engagement element connectable with a second mating surface of the bone fastener. Systems, spinal implants and methods are disclosed.

19 Claims, 13 Drawing Sheets

70 18 10 84 16 D1 12 14 56 62 20 22

(56) References Cited

U.S. PATENT DOCUMENTS 8,442,621 B2 5/2013 Gorek et al.
8,459,520 B2 6/2013 Giordano et al.
8,517,243 B2 8/2013 Giordano et al.
8,549,888 B2 10/2013 Isaacs
8,560,118 B2 10/2013 Greer et al.
8,652,120 B2 2/2014 Giordano et al.
8,659,591 B2 2/2014 Devane
8,684,253 B2 4/2014 Giordano et al.
8,709,016 B2 4/2014 Park et al.
8,738,181 B2 5/2014 Greer et al.
8,783,541 B2 7/2014 Shelton, IV et al.
8,805,003 B2 8/2014 Villain et al.
8,968,332 B2 3/2015 Farritor et al.
8,992,422 B2 3/2015 Spivey et al.
8,992,580 B2 3/2015 Bar et al.
9,078,685 B2 7/2015 Smith et al.
9,101,443 B2 8/2015 Bonutti
9,125,680 B2 8/2015 Kostrzewski et al.
9,119,655 B2 9/2015 Bowling et al.
9,131,986 B2 9/2015 Greer et al.
9,149,281 B2 10/2015 Bonutti
9,155,544 B2 10/2015 Bonutti
9,196,035 B2 11/2015 Weiss
9,211,145 B2 12/2015 Pereiro de Lamo et al.
9,220,570 B2 12/2015 Kim et al.
9,237,861 B2 1/2016 Nahum et al.
9,241,768 B2 1/2016 Sandhu et al.
9,241,771 B2 1/2016 Kostrzewski et al.
9,271,779 B2 3/2016 Bonutti
9,283,048 B2 3/2016 Kostrzewski et al.
9,301,759 B2 4/2016 Spivey et al.
9,308,050 B2 4/2016 Kostrzewski et al.
9,486,227 B2 11/2016 Bonutti
9,561,594 B2 2/2017 Yamaguchi
9,566,121 B2 2/2017 Staunton et al.
2008/0195081 A1 8/2008 Moll
2008/0218770 A1 9/2008 Moll et al.
2012/0253332 A1 10/2012 Moll
2013/0296868 A1 11/2013 Bonutti
2014/0171966 A1 6/2014 Giordano et al.
2014/0275955 A1 9/2014 Crawford et al.
2014/0378999 A1 12/2014 Crawford et al.
2015/0032116 A1* 1/2015 Jerke .................. A61B 17/8875 606/104
2015/0032164 A1 1/2015 Crawford et al.
2015/0057675 A1 2/2015 Akeel et al.
2015/0100067 A1 4/2015 Cavanagh et al.
2015/0196326 A1 7/2015 Bar et al.
2015/0223897 A1 8/2015 Kostrzewski et al.
2015/0282855 A1* 10/2015 Bess .................. A61B 17/8875 606/86 A
2015/0305817 A1 10/2015 Kostrzewski
2015/0335386 A1 11/2015 Smith et al.
2015/0366624 A1 12/2015 Kostrzewski et al.
2016/0008011 A1 1/2016 Kostrzewski
2016/0038238 A1 2/2016 Kostrzewski et al.
2016/0066957 A1* 3/2016 Biedermann ...... A61B 17/7076 606/272
2016/0081754 A1 3/2016 Kostrzewski et al.
2016/0128789 A1 5/2016 Kostrzewski et al.
2016/0151120 A1 6/2016 Kostrzewski et al.
2016/0235492 A1 8/2016 Morard et al.
2016/0235494 A1 8/2016 Shelton, IV et al.
2016/0242849 A9 8/2016 Crawford et al.
2016/0278818 A1 9/2016 Donner et al.
2016/0278870 A1 9/2016 Quaid et al.
2016/0331481 A1 11/2016 Bonutti
2016/0343273 A1 11/2016 Stuart et al.

* cited by examiner

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument comprises a first member including a drive engageable with a first mating surface of a bone fastener. A second member is rotatable relative to the first member and includes an engagement element connectable with a second mating surface of the bone fastener. In some embodiments, systems, spinal implants and methods are disclosed.

In one embodiment, the surgical instrument includes an outer tubular sleeve extending between a proximal end and a distal end. The distal end includes a drive engageable with a drive socket of a bone fastener shaft. An inner shaft is rotatable relative to the sleeve and includes a screw connectable with an inner threaded surface of a bone fastener receiver.

In one embodiment, a spinal implant system is provided. The spinal implant system comprises a surgical instrument including an outer tubular sleeve extending between a proximal end and a distal end. The distal end includes a drive engageable with a bone fastener shaft. An inner shaft of the surgical instrument is rotatable relative to the sleeve and includes a screw connectable with a threaded surface of a bone fastener receiver. An implant support includes extender tabs configured for engagement with the bone fastener receiver. A guide member includes an inner surface that defines a cavity configured for disposal of the sleeve and an image guide being oriented relative to a sensor to communicate a signal representative of a position of the guide member.

BRIEF DESCRIPTION OF THE DRAWINGS

The present disclosure will become more readily apparent from the specific description accompanied by the following drawings, in which.

DETAILED DESCRIPTION

Figure 1:
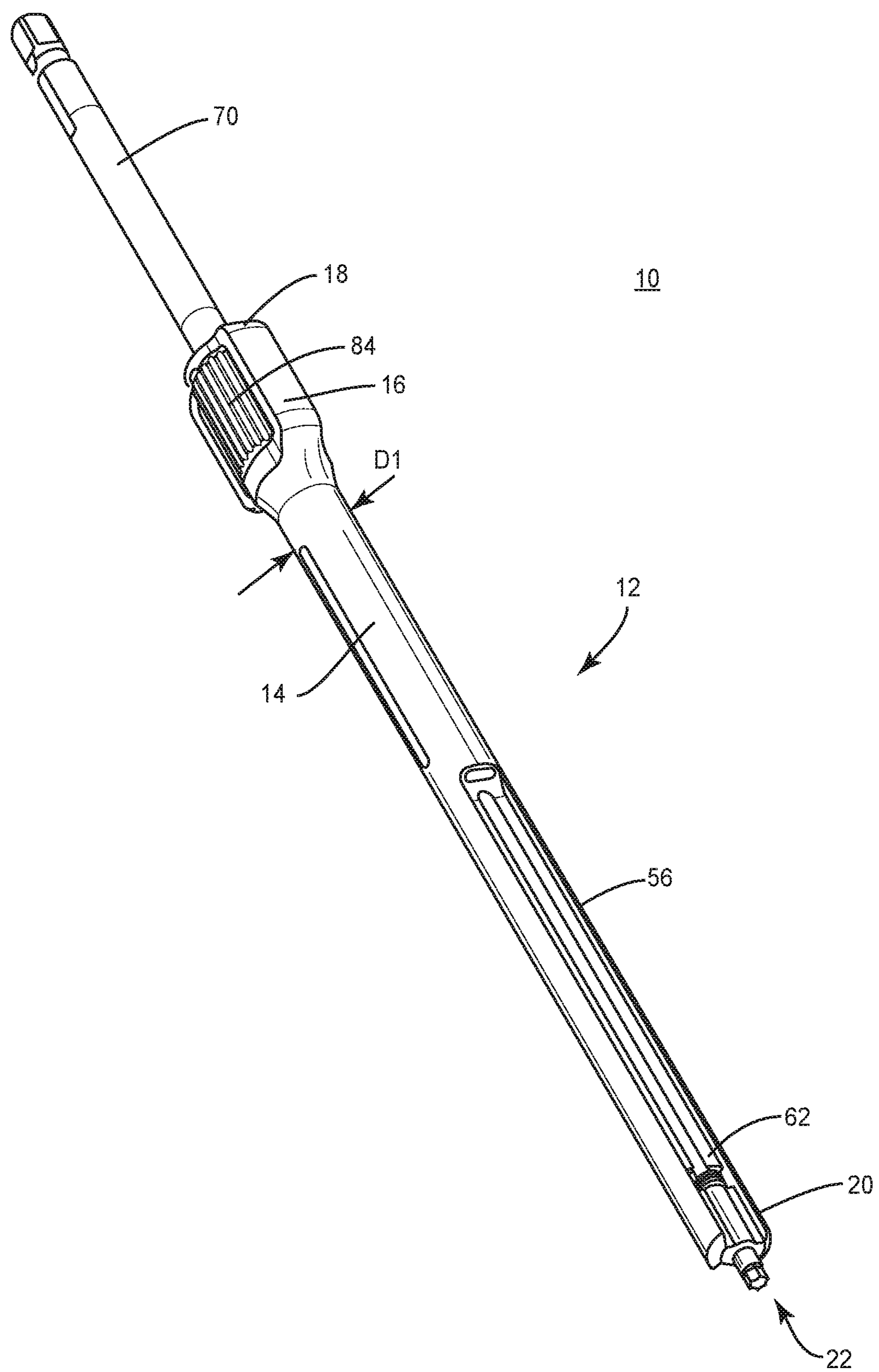
FIG. 1 is a perspective view of components of one embodiment of a surgical system in accordance with the principles of the present disclosure.
Figure 2:
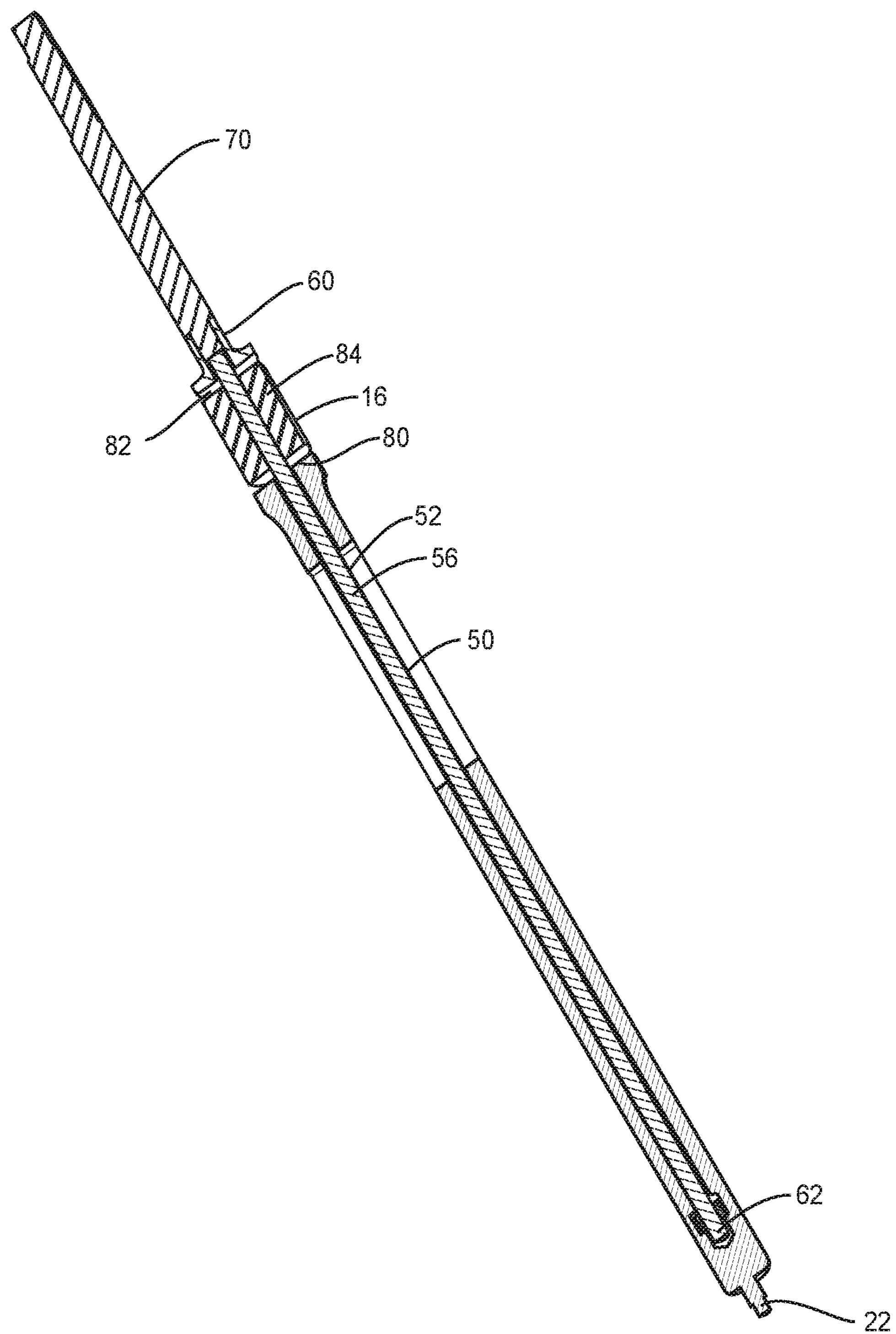
FIG. 2 is a cross section view of the components shown in FIG. 1.
Figure 3:
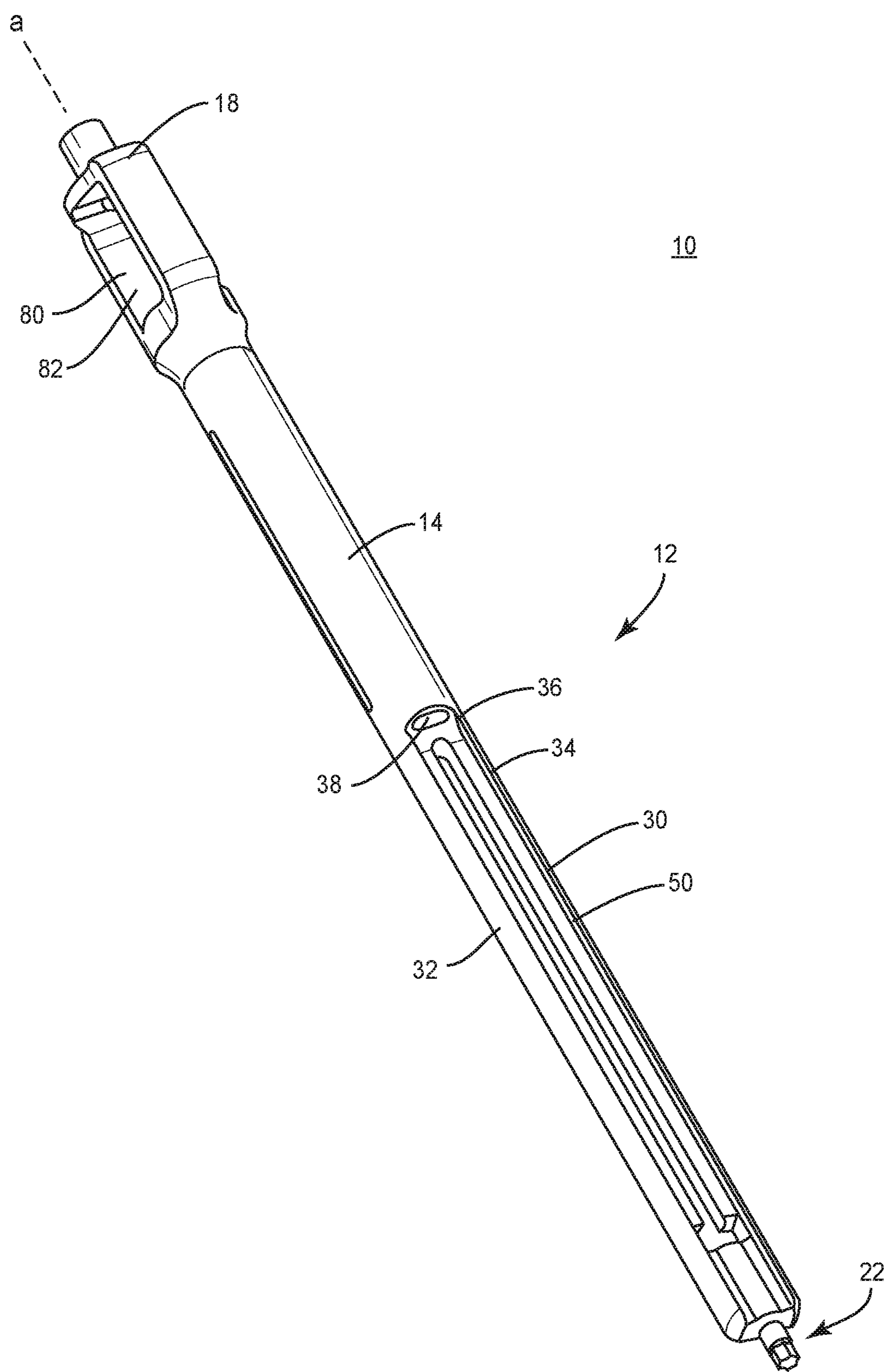
FIG. 3 is a perspective view of components of the system shown in FIG. 1.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system comprises a surgical instrument that comprises a screw driver that can be employed with bone fasteners and one or more implant supports, such as, for example, an extender, for treating a spine. In some embodiments, the present surgical system includes a surgical instrument that can easily connect and disconnect from a bone fastener. In some embodiments, an extender can be connected in alignment with the surgical instrument to facilitate manipulation. In some embodiments, the present surgical system includes a surgical instrument that can be employed with an end effector of a robotic arm to facilitate implant with the robotic arm. In some embodiments, the surgical instrument is guided through the end effector for a guide-wireless screw insertion. In some embodiments, the surgical instrument comprises a robot screw driver employed with robotic and/or navigation guidance, which may include an image guide.

In some embodiments, the present surgical system includes a screw driver having an outer shaft and a drive tip that engages a bone fastener. In some embodiments, the outer shaft and the drive tip are of one piece construction. In some embodiments, the one piece construction allows tolerances to be controlled tightly for improved accuracy of trajectory during implant insertion. In some embodiments, the drive tip includes a Torx configuration. In some embodiments, the present surgical system includes a screw driver having an internal retention mechanism. In some embodiments, the retention mechanism is fixed with a receiver of a bone fastener to resist and/or prevent disengagement of the retention mechanism from the receiver, for example, due to connection or friction with the end effector or tissue.

In some embodiments, the present surgical system includes a screw driver for use with robotic surgery. In some embodiments, the screw driver can be employed with fixed-axis screws (FAS), uni-axial screws (UAS), sagittal adjusting screws (SAS), transverse sagittal adjusting screws (TSAS) and multi-axial screws (MAS) screws, and allows the screws to be driven through a robotic end effector. In some embodiments, the screw driver includes a one piece outer sleeve having a tip. In some embodiments, the screw driver includes an internal retaining device that prevents accidental disengagement and/or unthreading.

In some embodiments, the present surgical system includes a screw driver including an outer shaft or sleeve having an outside diameter that is slightly larger than a screw spin diameter of a bone screw. This configuration allows the bone screw and the screw driver to pass through the end effector. In some embodiments, the screw driver includes a thumb wheel that is connected to a retention screw that threads into the bone screw. In some embodiments, the present surgical system includes tab extenders connected to the screw driver and prevented from extending outside the outside diameter of the screw driver by engaging undercuts of the screw driver. This configuration prevents an interference or hang-up if the bone screw needs to be removed through the end effector.

In some embodiments, the present surgical system includes a screw driver that is employed with a method of assembling components of the present system, which includes the step of connecting a bone screw to the screw driver. In some embodiments, the method includes the step of inserting a drive tip of the screw driver into a drive socket of a receiver of the bone screw while aligning tab extenders in mating grooves of the screw driver. In some embodiments, the method includes the step of rotating a thumb wheel actuator of the screw driver to tighten and pull the bone screw tight against the screw driver. In some embodiments, the method includes the step of inserting the retention screw and thumb wheel laterally with an outer shaft/sleeve of the screw driver. In some embodiments, the method includes sliding an inner shaft of the screw driver from a rear orientation. In some embodiments, the retention screw, thumb wheel and inner shaft include mating surfaces having a double D shape to transmit torque. In some embodiments, the method includes internal parts that are retained by inserting a quick connect shaft from a rear orientation and welding the quick connect shaft to the outer shaft.

In some embodiments, the present surgical system includes a screw driver that includes a quick connect shaft, an inner shaft, a thumb wheel, an outer driver shaft and a retention screw. The inner shaft, thumb wheel and retention screw include double D or hex shape mating surfaces. In some embodiments, the screw driver includes cleaning slots for flushing and/or cleaning. In some embodiments, the thumb wheel, retention screw and inner shaft freely float within the assembly. In some embodiments, the retention screw can freely translate axially relative to the inner shaft or up and down along the inner shaft. In some embodiments, the retention screw and the thumb wheel are keyed to a double-D configuration of the inner shaft. In some embodiments, the retention screw is axially translatable relative to the inner shaft between a first position, for example, a non-locking position prior to tightening, and a second position, for example, a locking position after tightening. In some embodiments, this configuration allows the drive tip to engage the bone screw prior to rotating the thumb wheel for tightening the screw driver to the bone screw.

In some embodiments, the surgical system includes an implant support, such as, for example, a collar and extender tabs. In some embodiments, the surgical system is employed with a method for treating spinal trauma and/or deformity disorders. In some embodiments, the surgical system is employed with a method for treating spinal trauma and/or deformity disorders with a minimally invasive surgical technique.

In some embodiments, the surgical system includes extender tabs. In some embodiments, the extender tabs are configured for aligning an implant, such as, for example, a bone fastener, with various instruments and providing an access path for set screws and rods. In some embodiments, the extender tabs are connectable with a SAS. In some embodiments, the surgical system facilitates sagittal correction and/or manipulation when a spinal implant, such as, for example, a spinal rod is disposed with a receiver. In some embodiments, the extender tabs are connectable with a TSAS. In some embodiments, the surgical system includes a receiver that is configured to accommodate transverse and sagittal anatomical differences.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-13, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, such as, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Spinal implant system 10 includes a surgical instrument, such as, for example, a driver 12. Driver 12 can be employed with an end effector 200 (FIG. 10) of a robotic arm R (FIG. 13) to facilitate implant with robotic arm R. Driver 12 is guided through end effector 200 for guide-wireless insertion of a spinal implant, such as, for example, a bone fastener 100, as described herein.

Driver 12 includes a member, such as, for example, an outer tubular sleeve 14. Outer sleeve 14 extends between a proximal end 18 and a distal end 20. Outer sleeve 14 defines a longitudinal axis a. In some embodiments, outer sleeve 14 may have various configurations including, for example, round, oval, polygonal, irregular, consistent, variable, uniform and non-uniform. Outer sleeve 14 includes a diameter D1. In some embodiments, diameter D1 is slightly larger than a screw spin diameter D2 of bone fastener 100. This configuration allows bone fastener 100 and driver 12 to pass through end effector 200 of the robotic arm, as described herein.

Figure 9A:
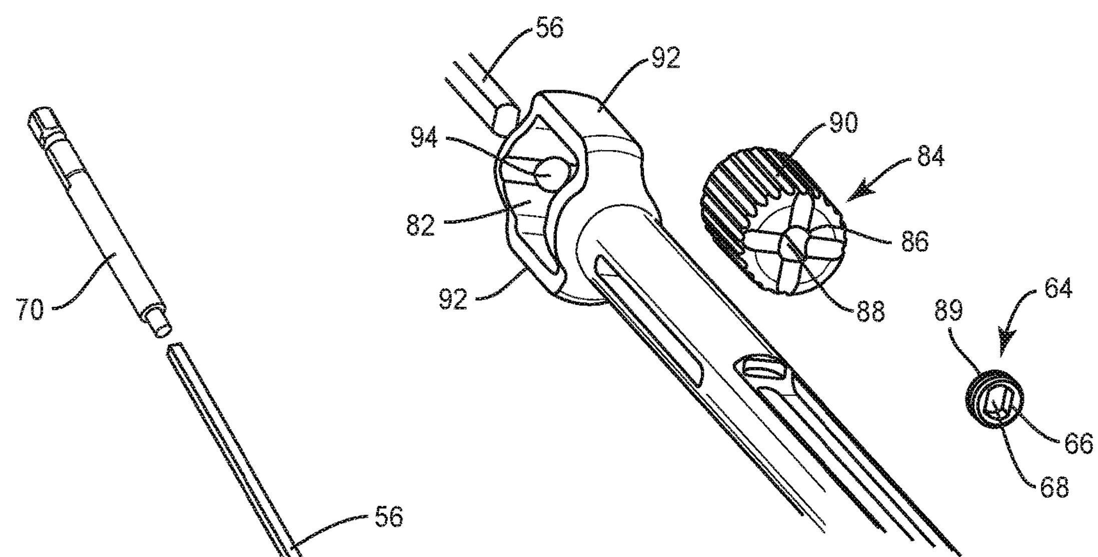
FIG. 9A is an enlarged view of detail A shown in FIG. 9.
Figure 9:
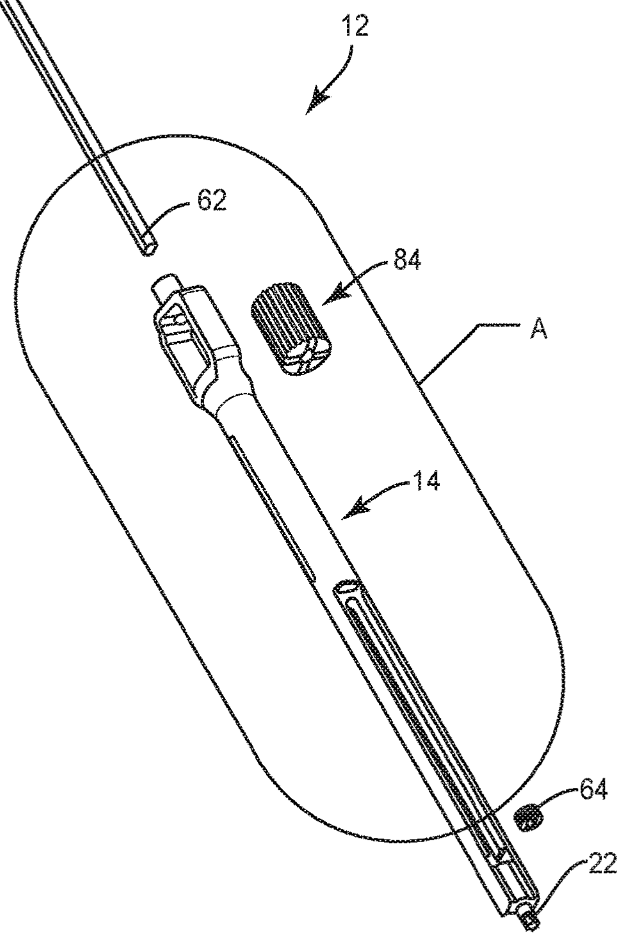
FIG. 9 is a perspective view of components of the system shown in FIG. 5 with parts separated.
Figure 10:
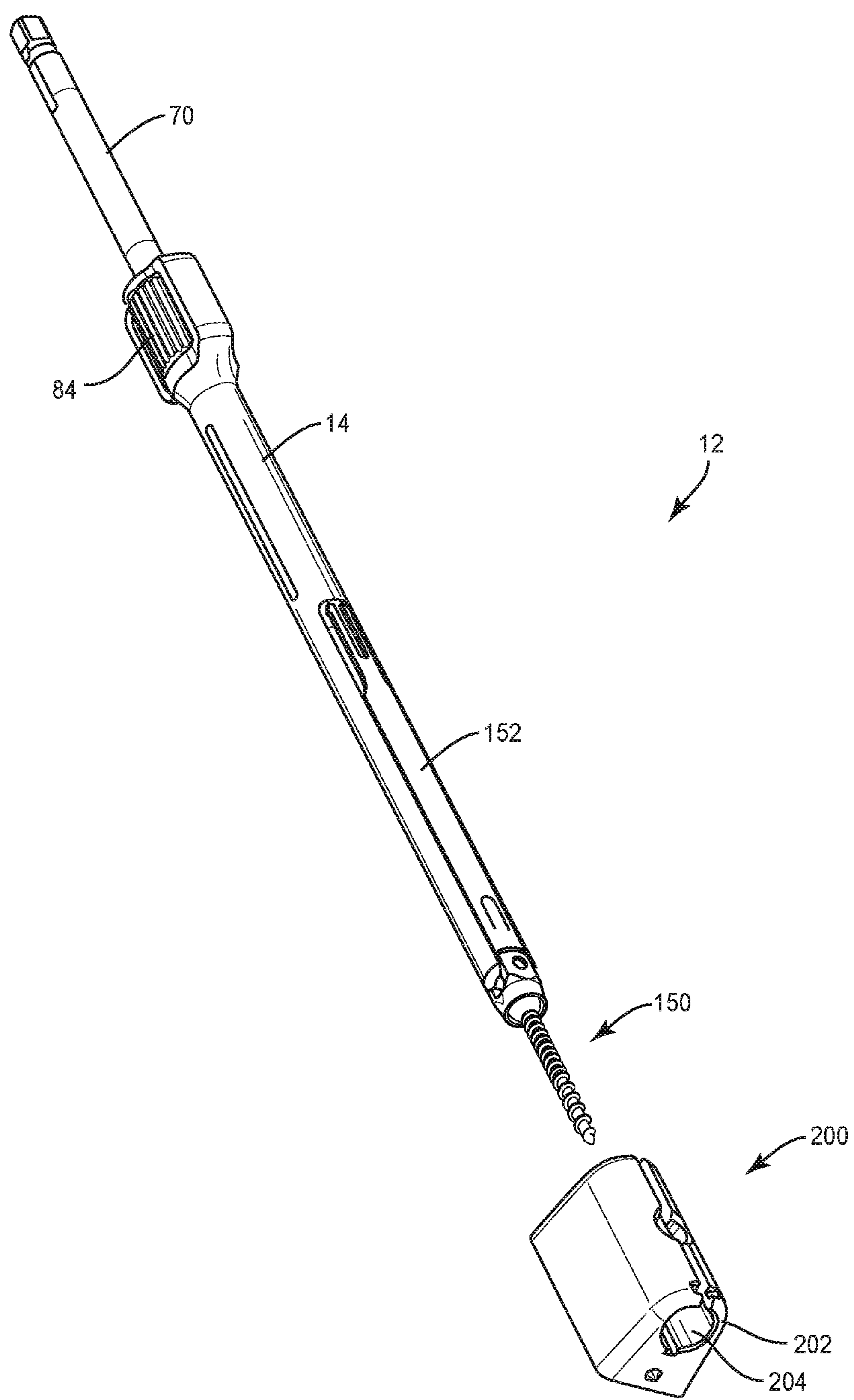
FIG. 10 is a perspective view of components of one embodiment of a surgical system in accordance with the principles of the present disclosure.
Figure 11:
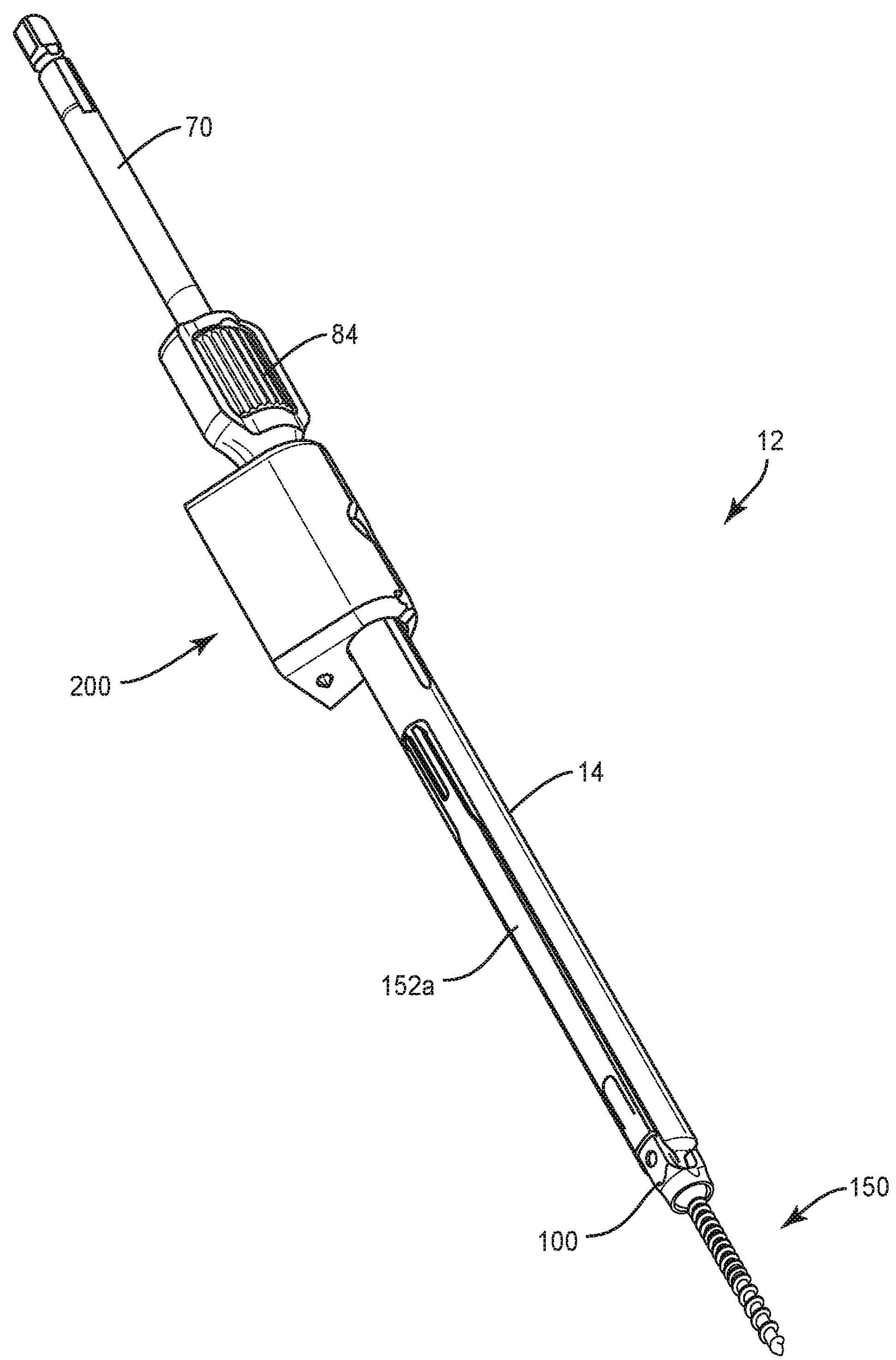
FIG. 11 is a perspective view of the components of the system shown in FIG. 10.

Outer sleeve 14 includes a surface 50 that defines a channel 52. Channel 52 is configured for disposal of a member, such as, for example, an inner shaft 56 and an engagement element, such as, for example, a screw 64, as described herein. Outer sleeve 14 includes a collar body 16 having a surface 80. Surface 80 defines a cavity 82. Body 16 includes bifurcated arms 92 disposed about cavity 82 to facilitate disposal and access to an actuator, such as, for example, a thumb wheel 84 therein. Body 16 includes opening 94 disposed at end 18. Opening 94 is in communication with cavity 82 and in alignment with channel 52 to facilitate insertion of inner shaft 56 into end 18, through wheel 84 and into channel 52 for assembly, as described herein. Wheel 84 is configured to actuate rotation of inner shaft 56 and screw 64, as described herein. Wheel 84 includes a surface 86 that defines a cavity 88. Cavity 88 is configured for disposal of a correspondingly shaped portion of inner shaft 56, as shown in FIGS. 9 and 9A.

Inner shaft 56 extends between an end 60 and an end 62. End 60 is engageable with wheel 84 for rotation of inner shaft 56 and screw 64, as described herein. Surface 86 engages end 60 in an interference fit to facilitate simultaneous rotation of wheel 84 and inner shaft 56. In some embodiments, surface 86 defines a double-D cross section for a mating engagement with correspondingly shaped end 60 of inner shaft 56. In some embodiments, cavity 88 includes various configurations, such as, for example, hexalobe, cruciform, phillips, square, hexagonal, polygonal, star cross sectional configuration for a mating engagement with correspondingly shaped portion of inner shaft 56. In some embodiments, wheel 84 includes a surface 90 configured to facilitate gripping of wheel 84, such as, for example a knurled surface.

Screw 64 includes an inner surface 66. Surface 66 defines a cavity 68 configured for disposal of a correspondingly shaped portion of end 62 of inner shaft 56. Surface 66 engages inner shaft 56 in an interference fit to facilitate simultaneous rotation of inner shaft 56 and screw 64, as described herein. In some embodiments, surface 66 defines a double-D cross section for a mating engagement with correspondingly shaped end 62. In some embodiments, cavity 68 includes various configurations, such as, for example, hexalobe, cruciform, phillips, square, hexagonal, polygonal, star cross sectional configuration for a mating engagement with a correspondingly shaped end 62. Screw 64 includes an outer surface having a thread form 89. Thread form 89 is configured for engagement with a mating surface, such as, for example, thread forms of arms 104, 106 of bone fastener 100 to pull and or draw bone fastener 100 into engagement with driver 12, as described herein.

Figure 12:
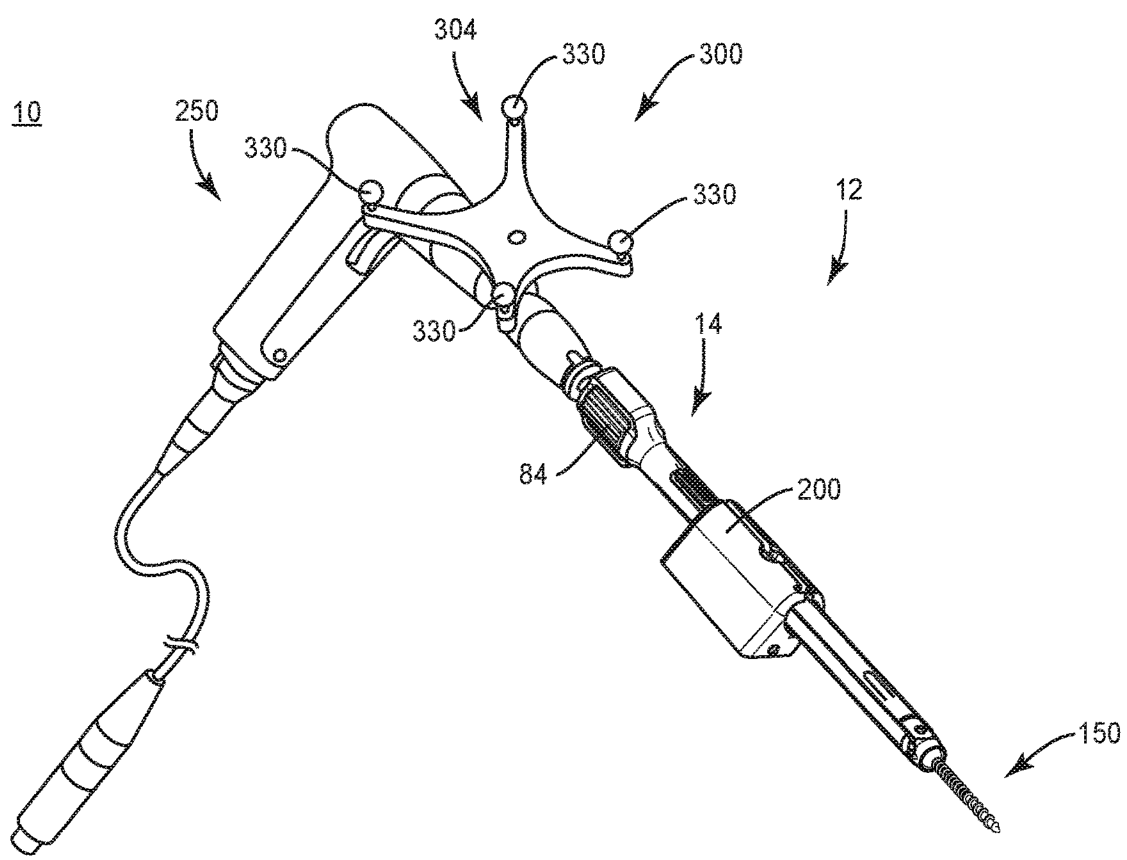
FIG. 12 is a perspective view of components of one embodiment of a surgical system in accordance with the principles of the present disclosure.

Inner shaft 56 and screw 64 are configured for movement relative to outer sleeve 14. Screw 64 is inserted laterally into channel 52. Wheel 84 is inserted laterally into cavity 82. With wheel 84 and screw 64 provisionally assembled with outer sleeve 14, inner shaft 56 is inserted from end 18, through opening 94, through cavity 88 and into channel 52 such that end 62 engages and passes through screw 64. Screw 64 is disposed with inner shaft 56 and wheel 84 is disposed with collar body 16, within channel 52, for assembly of the components of driver 12. A shaft 70 is inserted and attached with end 18 to assemble and retain inner shaft 56, wheel 84, screw 64 within channel 52 in a relatively movable configuration with outer sleeve 14, as described herein. In some embodiments, shaft 70 is attached with end 18 such that inner shaft 56, wheel 84, screw 64 freely slide, translate, rotate and/or float within channel 52. Inner shaft 56 retains screw 64 and wheel 84 with sleeve 14. In some embodiments, shaft 70 is welded with outer sleeve 14. In some embodiments, shaft 70 is configured to facilitate connection of driver 12 with a surgical instrument, such as, for example, an actuator/drill 250, as shown in FIG. 12. In some embodiments, shaft 70 includes quick connect surfaces or keyed geometry, such as, for example, triangle, hex, square or hexalobe to facilitate connection with actuator 250.

Figure 4:
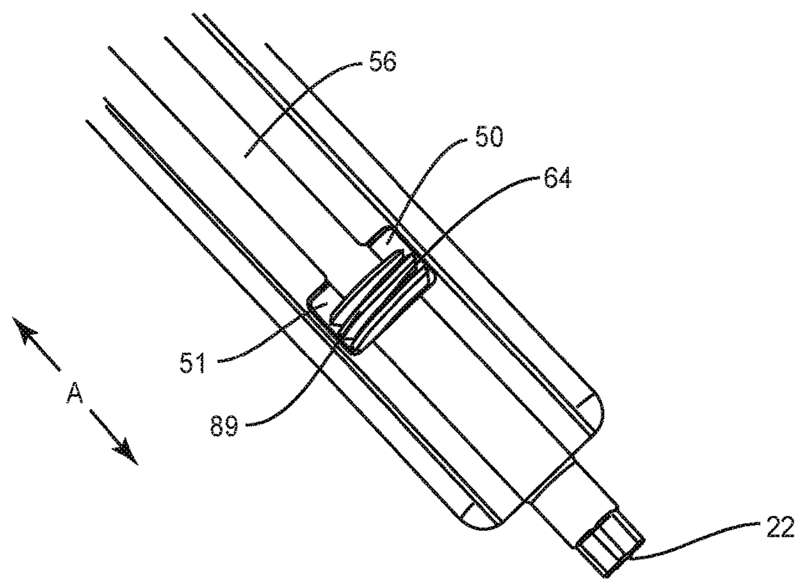
FIG. 4 is a break away view of components of the system shown in FIG. 1.

End 20 of outer sleeve 14 includes a distal tip, such as, for example, drive 22, as shown in FIG. 4. Drive 22 is integrally connected or monolithically formed with outer sleeve 14. This configuration facilitates control of tolerances to optimize accuracy of the connection of outer sleeve 14 with bone fastener 100. Drive 22 is engageable with a spinal implant, such as, for example, bone fastener 100. For example, drive 22 fits with and is engageable with a mating surface, such as, for example, a socket 110 of bone fastener 100. Rotation of outer sleeve 14 simultaneously rotates drive 22 to drive, torque, insert or otherwise connect bone fastener 100 with tissue, as described herein. In some embodiments, drive 22 includes a hexalobe geometry for a mating engagement with a correspondingly shaped socket 110. In some embodiments, drive 22 can alternatively include a cruciform, phillips, square, hexagonal, polygonal, star cross sectional configuration for disposal of a correspondingly shaped socket 110.

Outer sleeve 14 includes an extension 30 and an extension 32. Extensions 30, 32 include a wall 34 having a surface 36. Surface 36 is connectable with an implant support, such as, for example, extender tab 152, as described herein. Surface 36 defines a mating groove, such as, for example, a pocket 38 configured for engagement with extender tab 152, as described herein. Surface 36 is configured to resist and/or prevent disengagement of extender tab 152 from pocket 38, as described herein.

Extensions 30, 32 include a wall 40 having a surface 42. Surface 42 is connectable with extender tab **152*a*, as described herein. Surface 42 defines a mating groove, such as, for example, a pocket 44 configured for engagement with extender tab 152*a*, as described herein. Surface 42 is configured to resist and/or prevent disengagement of extender tab 152*a* from pocket 44**, as described herein.

Figure 5:
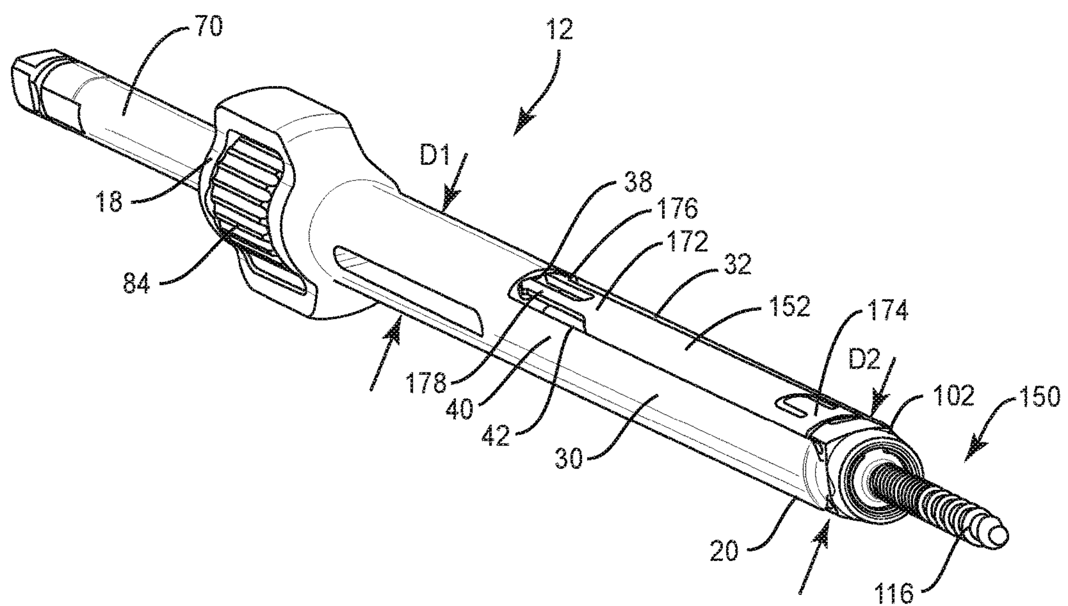
FIG. 5 is a perspective view of components of one embodiment of a surgical system in accordance with the principles of the present disclosure.
Figure 6:
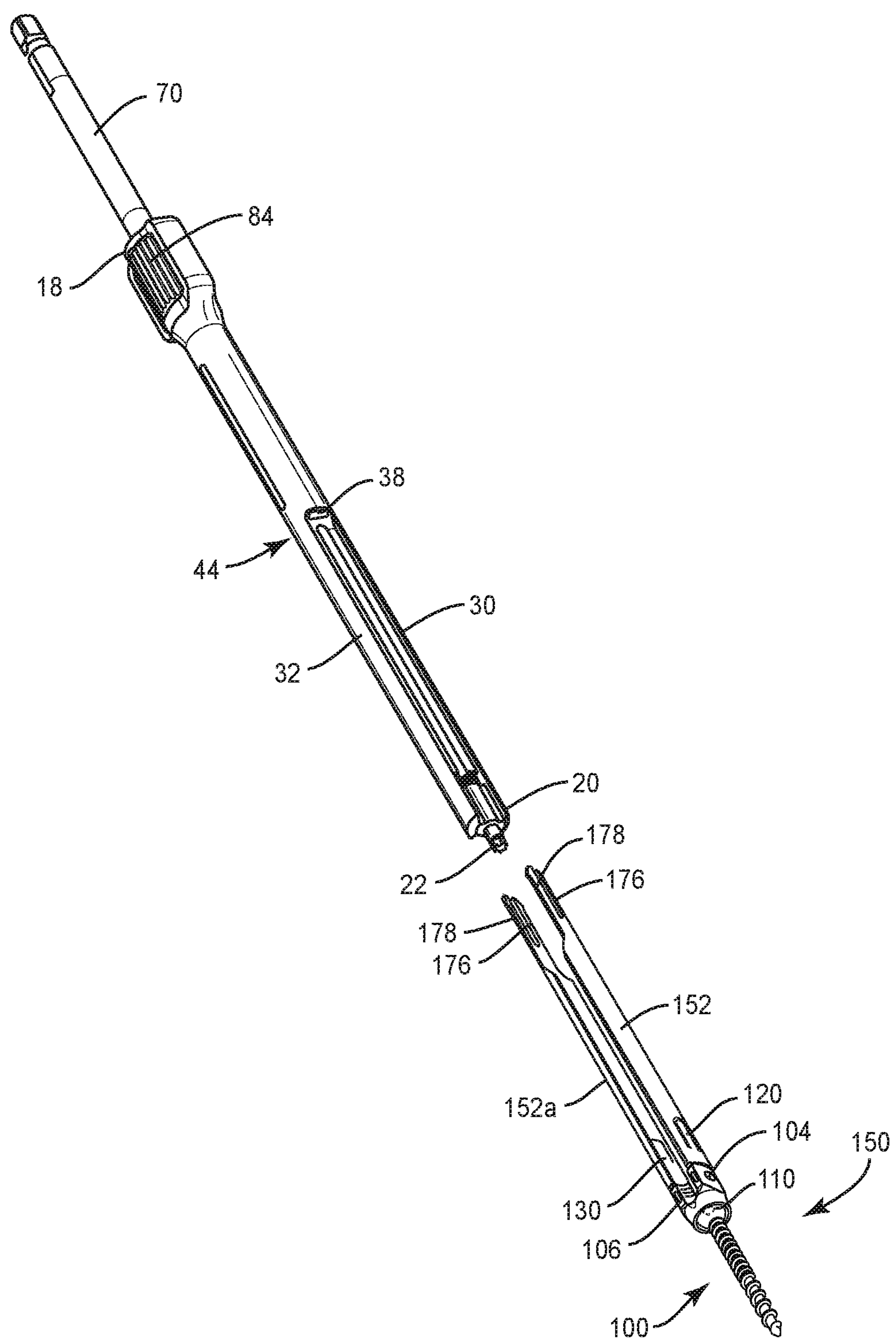
FIG. 6 is a perspective view of components of the system shown in FIG. 5 with parts separated.
Figure 7:
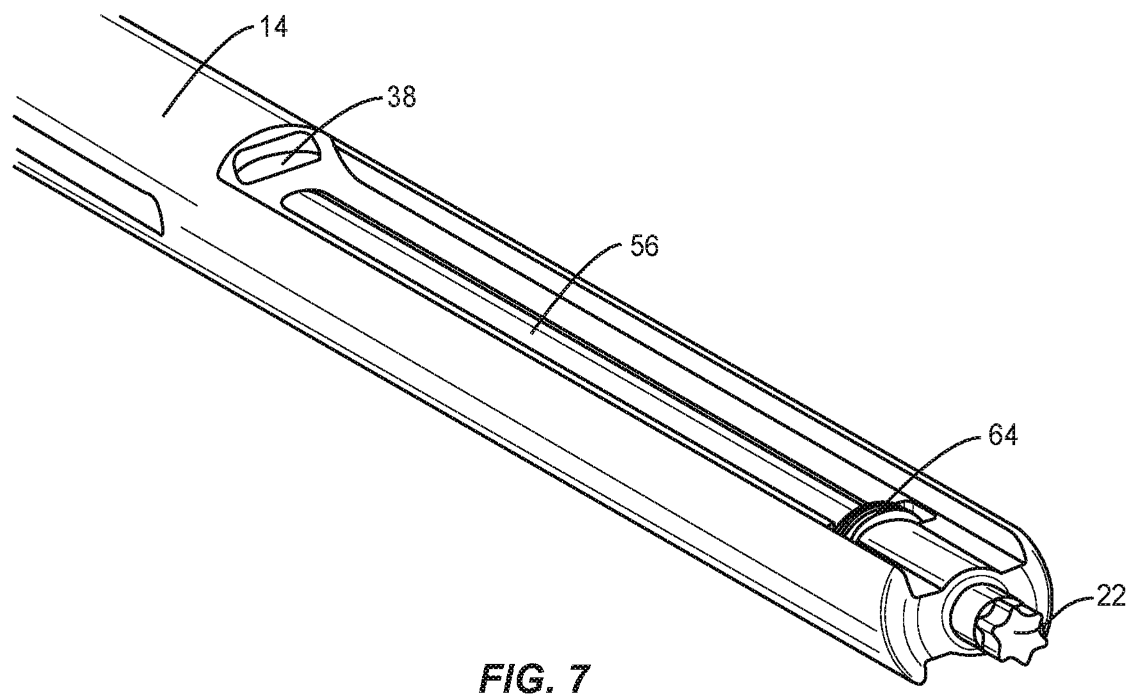
FIG. 7 is a break away view of components of the system shown in FIG. 6.
Figure 8:
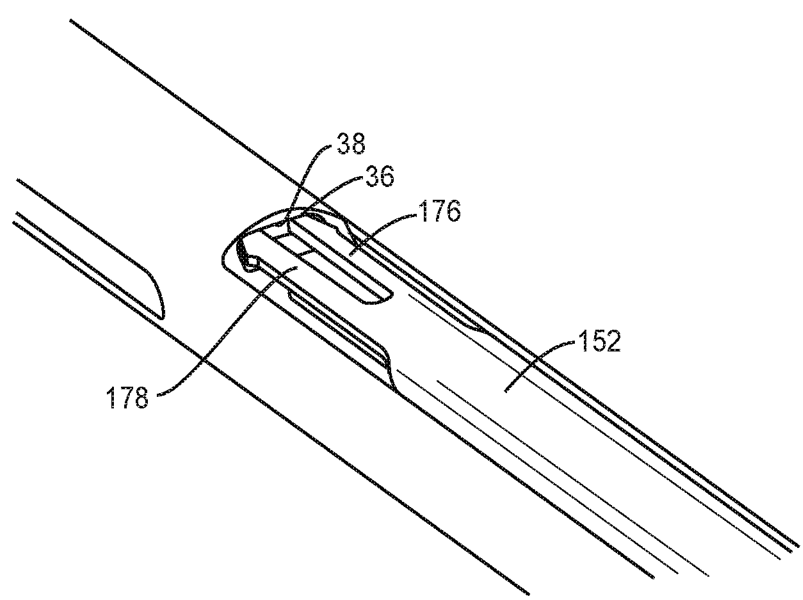
FIG. 8 is a break away view of components of the system shown in FIG. 5.

Pockets 38, 44 are configured for engagement with extender tabs 152, **152*a*, as shown in FIGS. 5 and 8. Disposal of extender tabs 152, 152*a* with pockets 38, 44 is configured to resist and/or prevent extender tabs 152, 152*a* from increasing diameter D1 when engaged with driver 12. In some embodiments, pockets 38, 44 are disposed parallel to axis a. In some embodiments, pockets 38, 44** are disposed at alternate orientations relative to axis a, such as, for example, at transverse, perpendicular and/or other angular orientations such as acute or obtuse, and/or may be offset or staggered.

Bone fastener 100 includes receiver 102. Receiver 102 extends along axis a when connected with outer sleeve 14.

Receiver 102 includes a pair of spaced apart arms 104, 106 that define an implant cavity configured for disposal of a component of a spinal construct, such as, for example, a spinal rod (not shown). Receiver 106 includes socket 110 configured for engagement with drive 22, as described herein. Receiver 108 includes an inner surface having a thread form located adjacent arm 104 and a thread form located adjacent arm 106. The thread forms of arms 104, 106 are configured for engagement with thread form 89 to retain bone fastener 100 with driver 12, as described herein. Bone fastener 100 includes a threaded shaft 116. Shaft 116 is configured to penetrate tissue, such as, for example, bone.

Arm 104 includes a break away tab 120 that is frangibly connected to arm 104 such that manipulation of tab 120 relative to arm 104 can fracture and separate tab 120 from arm 104 at a predetermined force and/or torque limit, as described herein. Arm 106 includes a break away tab 130 that is frangibly connected to arm 106 such that manipulation of tab 130 relative to arm 106 can fracture and separate tab 130 from arm 106 at a predetermined force and/or torque limit, as described herein. In some embodiments, as force and/or torque is applied to tabs 120, 130 and resistance increases, for example, the predetermined torque and force limit is approached.

In some embodiments, tabs 120, 130 can fracture and separate at a predetermined force or torque limit, which may be in a range of approximately 2 Newton meters (N-m) to 8 N-m. In some embodiments, tabs 120, 130 and arms 104, 106 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of tabs 120, 130.

A bone fastener assembly 150 includes extender tabs 152, 152*a* connected with bone fastener 100. Extender tabs 152, 152*a* extend between a proximal end 172 and a distal end 174. Proximal end 172 includes spring tips 176, 178, as shown in FIG. 8. Spring tips 176, 178 are aligned and disposable with pockets 38, 44. Surfaces 36, 42 are configured to resist and/or prevent disengagement of spring tips 176, 178, as described herein. Distal ends 174 are configured for slidable disposal of a portion of bone fastener 100, such as, for example, tabs 120, 130. In some embodiments, tabs 120, 130 are configured to releasably fix extender tabs 152, 152*a* with bone fastener 100 for connection with outer sleeve 14.

In use, bone fastener assembly 150 is connected with driver 12, as described herein, and drive 22 is oriented for engagement with socket 110. Drive 22 is engaged with socket 110 and screw 64 is disposed with inner shaft 56 and assembled with outer sleeve 14 for axial translation relative to outer sleeve 14 and along inner shaft 56 between a non-locking configuration, as shown in FIG. 4, and a locking configuration, as shown in FIG. 5, with a spinal implant, such as, for example, bone fastener 100. In the non-locking configuration, screw 64 is freely translatable relative to inner shaft 56 within an opening 51 of channel 52, in the direction shown by arrows A in FIG. 4, and rotatable relative to outer sleeve 14. This configuration allows drive 22 to engage socket 110 prior to fixation of screw 64 with bone fastener 100.

With bone fastener assembly 150 connected with outer sleeve 14, thread form 89 is aligned with the thread forms of arms 104, 106 for engagement therebetween to retain bone fastener 100 with driver 12. Screw 64 is keyed with the double D cross section of end 62 for simultaneous rotation with inner shaft 56 and wheel 84. Wheel 84 is manipulated for rotation such that inner shaft 56 rotates screw 64 relative to and independent of outer sleeve 14. Thread form 89 engages the thread forms of arms 104, 106 and screw 64 axially translates into receiver 102 and relative to inner shaft 56. The threaded engagement of screw 64 and receiver 102 pulls and/or draws bone fastener 100 into the locking configuration with driver 12 for releasable fixation therebetween. Drive 22 is connected with outer sleeve 14, as described herein, and outer sleeve 14 is rotated to drive, torque, insert or otherwise connect bone fastener 100 with adjacent tissue. Screw 64 remains releasably fixed with receiver 102, independent of outer sleeve 14 rotation and/or engagement or friction with components of spinal implant system 10 as described herein, to resist and/or prevent disengagement or unthreading of screw 64 from receiver 102.

Figure 13:
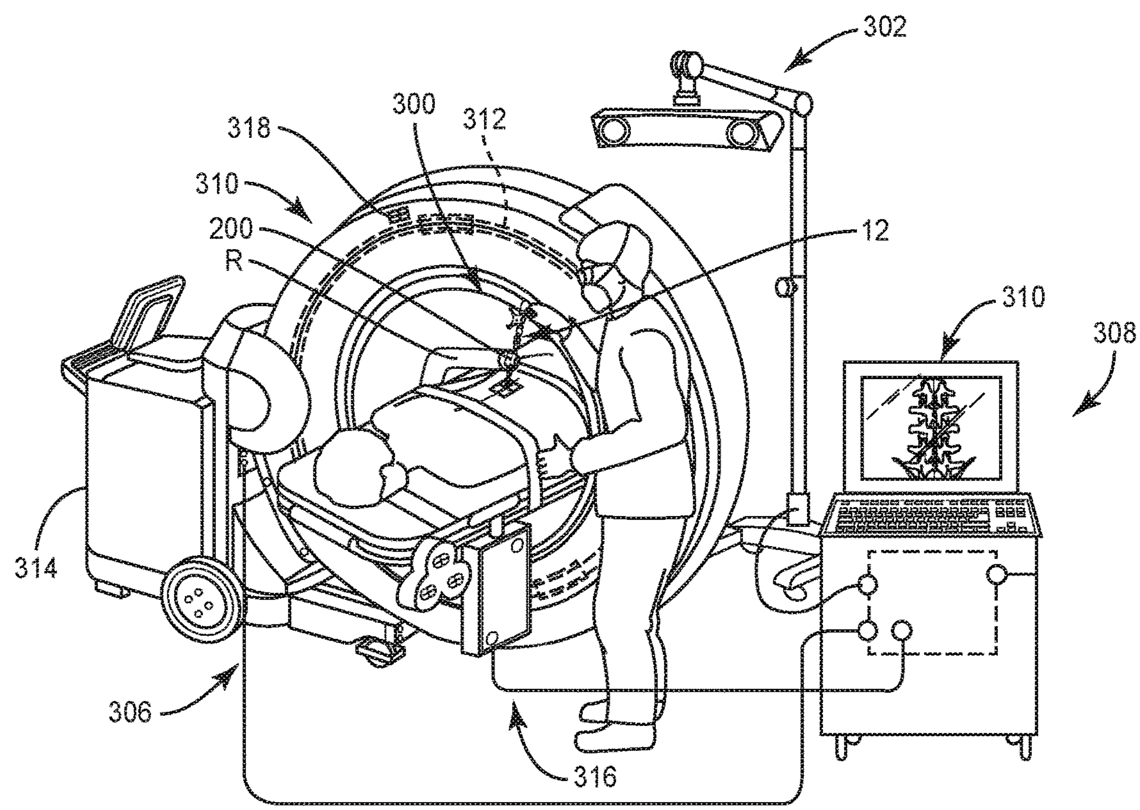
FIG. 13 is a perspective view of components one embodiment of a surgical system in accordance with the principles of the present disclosure.

In some embodiments, driver 12 includes a navigation component 300, as shown in FIGS. 12 and 13. Driver 12 is configured for disposal adjacent a surgical site such that navigation component 300 is oriented relative to a sensor array 302 to facilitate communication between navigation component 300 and sensor array 302 during a surgical procedure, as described herein. Navigation component 300 is configured to generate a signal representative of a position of bone fastener 100 relative to driver 12 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals. In some embodiments, navigation component 300 is connected with shaft 70 or outer sleeve 14 via an integral connection, friction fit, pressure fit, interlocking engagement, mating engagement, dovetail connection, clips, barbs, tongue in groove, threaded, magnetic, key/keyslot and/or drill chuck.

Navigation component 300 includes an emitter array 304. Emitter array 304 is configured for generating a signal to sensor array 302 of a surgical navigation system 306, as shown in FIG. 13 and described herein. In some embodiments, the signal generated by emitter array 304 represents a position of bone fastener 100 relative to driver 12 and relative to tissue, such as, for example, bone. In some embodiments, the signal generated by emitter array 304 represents a three dimensional position of bone fastener 100 relative to tissue.

In some embodiments, sensor array 302 receives signals from emitter array 304 to provide a three-dimensional spatial position and/or a trajectory of bone fastener 100 relative to driver 12 and/or tissue. Emitter array 304 communicates with a processor of computer 308 of navigation system 306 to generate data for display of an image on monitor 310, as described herein. In some embodiments, sensor array 302 receives signals from emitter array 304 to provide a visual representation of a position of bone fastener 100 relative to driver 12 and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 306 is configured for acquiring and displaying medical imaging, such as, for example, x-ray images appropriate for a given surgical procedure. In some embodiments, pre-acquired images of a patient are collected. In some embodiments, surgical navigation system 306 can include an O-arm® imaging device 310 sold by Medtronic Navigation, Inc. having a place of business in Louisville, Colo., USA. Imaging device 310 may have a generally annular gantry housing that encloses an image capturing portion 312.

In some embodiments, navigation system 306 comprises an image capturing portion 314 that may include an x-ray source or emission portion and an x-ray receiving or image receiving portion located generally or as practically possible 180 degrees from each other and mounted on a rotor (not shown) relative to a track of image capturing portion 314. Image capturing portion 314 can be operable to rotate 360 degrees during image acquisition. Image capturing portion 314 may rotate around a central point or axis, allowing image data of the patient to be acquired from multiple directions or in multiple planes. Surgical navigation system 306 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 306 can include C-arm fluoroscopic imaging systems, which can generate three-dimensional views of a patient. The position of image capturing portion 314 can be precisely known relative to any other portion of an imaging device of navigation system 306. In some embodiments, a precise knowledge of the position of image capturing portion 314 can be used in conjunction with a tracking system 316 to determine the position of image capturing portion 314 and the image data relative to the patient.

Tracking system 316 can include various portions that are associated or included with surgical navigation system 306. In some embodiments, tracking system 316 can also include a plurality of types of tracking systems, such as, for example, an optical tracking system that includes an optical localizer, such as, for example, sensor array 302 and/or an EM tracking system that can include an EM localizer. Various tracking devices can be tracked with tracking system 316 and the information can be used by surgical navigation system 306 to allow for a display of a position of an item, such as, for example, a patient tracking device, an imaging device tracking device 318, and an instrument tracking device, such as, for example, emitter array 304, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville; Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted a computer 314 where they may be forwarded to computer 308. Image transfer may be performed over a standard video connection or a digital link including wired and wireless. Computer 308 provides the ability to display, via monitor 310, as well as save, digitally manipulate, or print a hard copy of the received images. In some embodiments, images may also be displayed to the surgeon through a heads-up display.

In some embodiments, surgical navigation system 306 provides for real-time tracking of the position of bone fastener 100 relative to driver 12 and/or tissue can be tracked. Sensor array 302 is located in such a manner to provide a clear line of sight with emitter array 304, as described herein. In some embodiments, fiducial markers 330 of emitter array 304 communicate with sensor array 302 via infrared technology. Sensor array 302 is coupled to computer 308, which may be programmed with software modules that analyze signals transmitted by sensor array 302 to determine the position of each object in a detector space.

Driver 12 is configured for use with an end effector 200 of a robotic arm R. End effector 200 includes a surface 202 that defines a cavity, such as, for example, a channel 204. Channel 204 is configured for passage of bone fastener assembly 150 and disposal of driver 12. Robotic arm R includes position sensors (not shown), similar to those referenced herein, which measure, sample, capture and/or identify positional data points of end effector 200 in three dimensional space for a guide-wireless insertion of bone fasteners 100 with selected vertebral levels. In some embodiments, the position sensors of robotic arm R are employed in connection with surgical navigation system 306 to measure, sample, capture and/or identify positional data points of end effector 200 in connection with surgical treatment, as described herein. The position sensors are mounted with robotic arm R and calibrated to measure positional data points of end effector 200 in three dimensional space, which are communicated to computer 308.

In assembly, operation and use, spinal implant system 10, similar to the systems and methods described herein, is employed with a surgical procedure, such as, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. Spinal implant system 10 may be completely or partially revised, removed or replaced.

In use, to treat vertebrae (not shown), a medical practitioner obtains access to a surgical site in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby the vertebrae is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of the vertebrae as well as for aspiration and irrigation of a surgical region.

Pilot holes (not shown) are made in selected levels of vertebrae for receiving bone fasteners 100. Bone fastener assembly 150 is connected with driver 12, as described herein. Drive 22 is engaged with socket 110 and screw 64 is disposed in a non-locking configuration, as described herein, such that screw 64 is freely translatable relative to inner shaft 56 within an opening 51 of channel 52 and rotatable relative to outer sleeve 14. With bone fastener assembly 150 connected with outer sleeve 14, wheel 84 is manipulated for rotation such that inner shaft 56 rotates screw 64 relative to and independent of outer sleeve 14, as described herein. Threaded engagement of screw 64 and receiver 102 pulls and/or draws bone fastener 100 into the locking configuration with driver 12 for releasable fixation therebetween.

Driver 12, connected with bone fastener assembly 150, is oriented for disposal with end effector 200 of robotic arm R, as described herein. The assembly of driver 12/bone fastener assembly 150 are disposed with channel 204 for implantation of bone fasteners 100 with vertebrae employing robotic arm R and/or surgical navigation system 306, as described herein. Actuator 250 is connected with shaft 70 and drive 22 engages bone fastener 100, as described herein, and outer sleeve 14 is rotated to drive, torque, insert or otherwise connect bone fastener 100 with adjacent tissue. Screw 64 remains releasably fixed with receiver 102, independent of outer sleeve 14 rotation and/or engagement or friction with end effector 200 to resist and/or prevent disengagement or unthreading of screw 64 from receiver 102. In some embodiments, driver 12 is manipulated to deliver one or more bone fasteners 100 to a surgical site including vertebrae. Sensor array 302 receives signals from navigation component 300 to provide a three-dimensional spatial position and/or a trajectory of the assembly of driver 12/bone fastener assembly 150, which may be disposed with end effector 200, relative to vertebrae and/or components of spinal implant system 10 for display on monitor 310.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone fasteners for use with a single vertebral level or a plurality of vertebral levels.

In some embodiments, one or more bone fasteners, as described herein, may be engaged with tissue in various orientations, such as, for example, series, parallel, offset, staggered and/or alternate vertebral levels. In some embodiments, the bone fasteners may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 14:
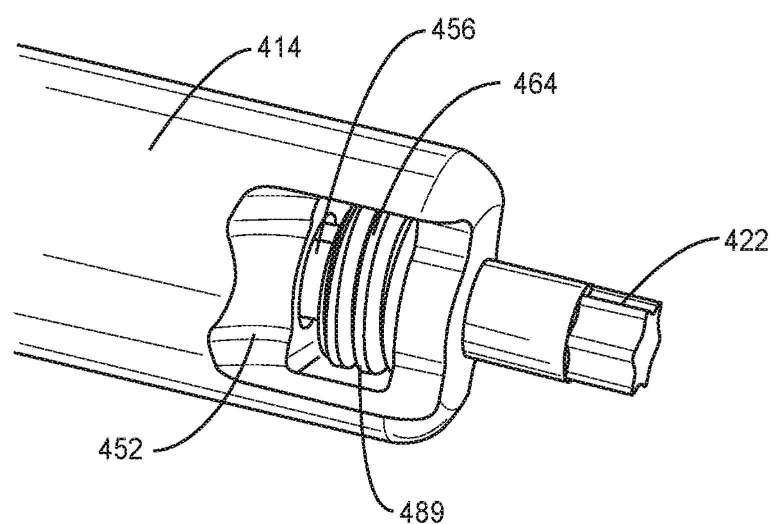
FIG. 14 is a break away view of components of one embodiment of a surgical system in accordance with the principles of the present disclosure.
Figure 15:
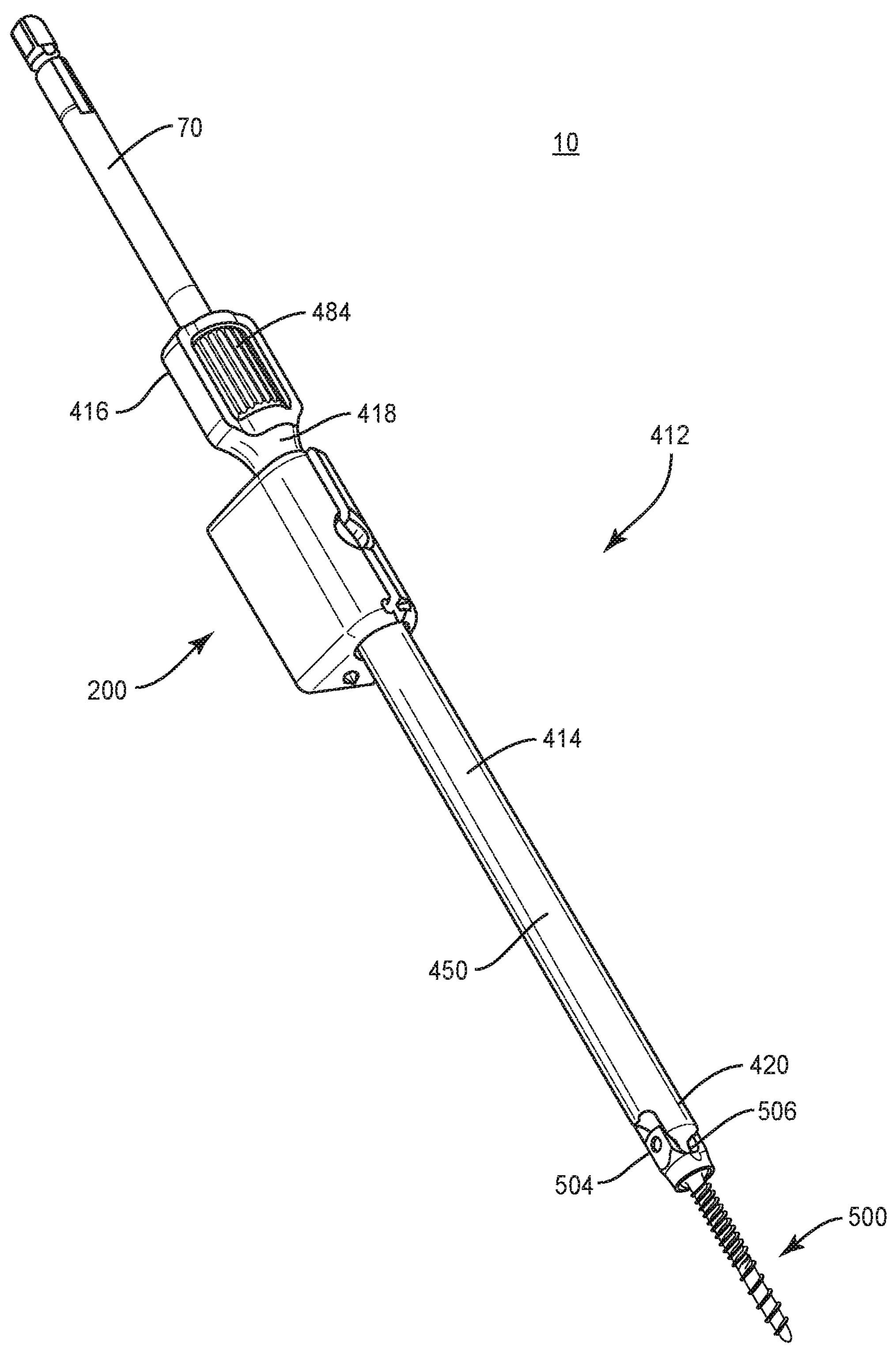
FIG. 15 is a perspective view of components of one embodiment of a surgical system in accordance with the principles of the present disclosure.

In some embodiments, as shown in FIGS. 14 and 15, spinal implant system 10, similar to the systems and methods described herein, includes a driver 412, similar to driver 12 described herein. Driver 412 is configured for connection with a multi-axial screw (MAS) 500. Driver 412 can be employed with end effector 200 and/or surgical navigation system 306, as described herein, for guide-wireless insertion of MAS 500 with tissue, similar to that described herein.

Driver 412 includes an outer sleeve 414. Outer sleeve 414 extends between a proximal end 418 and a distal end 420. Outer sleeve 414 includes a continuous and non-interrupted outer surface 450 that extends between ends 418, 420. Surface 450 defines an interior channel 452. Channel 452 is configured for disposal of an inner shaft 456, similar to inner shaft 56, and a screw 464, similar to screw 64 described herein. Outer sleeve 414 includes a collar body 416, similar to collar body 16 described herein, to facilitate disposal and access to a thumb wheel 484, similar to wheel 84 described herein.

Inner shaft 456 is engageable with wheel 484 for rotation of inner shaft 456 and screw 464, similar to that described herein. Screw 464 includes an outer surface having a thread form 489 configured for engagement with thread forms of arms 504, 506 of MAS 500 to pull and/or draw MAS 500 into engagement with driver 412, as described herein. Inner shaft 456 and screw 464 are configured for movement relative to outer sleeve 414. A shaft 470, similar to shaft 70 described herein, is inserted and attached with outer sleeve 414 to assemble and retain inner shaft 456, wheel 484, screw 464 within channel 452 in a relatively movable configuration with outer sleeve 414, similar to that described herein.

End 420 of outer sleeve 414 includes a distal tip, such as, for example, drive 422, similar to drive 22 described herein. Drive 422 is integrally connected or monolithically formed with outer sleeve 414 and fits with and is engageable with a mating surface, such as, for example, a socket (not shown) of MAS 500, similar to that described herein. Rotation of outer sleeve 414 simultaneously rotates drive 422 to drive, torque, insert or otherwise connect MAS 500 with tissue, similar to that described herein.

In use, drive 422 is oriented for engagement with the socket of MAS 500. Drive 422 is engaged with the socket of MAS 500 and screw 464 is disposed with inner shaft 456 and assembled with outer sleeve 414 for axial translation relative to outer sleeve 414 and along inner shaft 456 between a non-locking configuration and a locking configuration, with MAS 500, similar to that described herein. In the non-locking configuration, screw 464 is freely translatable relative to inner shaft 456 and rotatable relative to outer sleeve 414. With MAS 500 connected with outer sleeve 14, thread form 489 is aligned with the thread forms of arms 504, 506 to retain MAS 500 with driver 412. Wheel 484 is manipulated for rotation such that inner shaft 456 rotates screw 464 relative to and independent of outer sleeve 414. Thread form 489 engages the thread forms of arms 504, 506 and screw 464 axially translates into the receiver of MAS 500 and relative to inner shaft 456. The threaded engagement of screw 464 and the receiver of MAS 500 pulls and/or draws MAS 500 into the locking configuration with driver 412 for releasable fixation therebetween. Drive 422 is connected with outer sleeve 414, as described herein, and outer sleeve 414 is rotated to drive, torque, insert or otherwise connect MAS 500 with adjacent tissue. Screw 464 remains releasably fixed with the receiver of MAS 500, independent of outer sleeve 414 rotation and/or engagement or friction with components of spinal implant system 10, as described herein, to resist and/or prevent disengagement or unthreading of screw 464 from the receiver of MAS 500.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:

a first member including a drive engageable with a shaft of a bone fastener;

a second member being rotatable relative to the first member and including a screw connectable with a receiver of the bone fastener;

an implant support including extender tabs configured for engagement with the receiver; and a guide member including an inner surface defining a cavity configured for disposal of a sleeve of the first member, the guide member including an image guide oriented relative to a sensor to communicate a signal representative of a position of the guide member, wherein the screw is axially translatable relative to an inner shaft of the second member between a non-locking configuration and a locking configuration with a threaded surface of the bone fastener receiver.

2. A surgical instrument as recited in claim 1, wherein the drive is integrally connected with the first member.

3. A surgical instrument as recited in claim 1, wherein the drive comprises a distal tip of the first member and is configured for disposal in a drive socket of the shaft.

4. A surgical instrument as recited in claim 1, wherein the first member includes a wall surface connectable with the implant support.

5. A surgical instrument as recited in claim 4, wherein the wall surface includes mating grooves that are engageable with the extender tabs.

6. A surgical instrument as recited in claim 4, wherein the wall surface defines a pocket surface engageable with proximal spring tips of the implant support.

7. A surgical instrument as recited in claim 1, wherein the sleeve defines an inner cavity configured for disposal of the inner shaft.

8. A surgical instrument as recited in claim 7, wherein the second member includes a rotatable actuator connected with the inner shaft.

9. A surgical instrument as recited in claim 8, wherein the rotatable actuator includes a knurled wheel including an inner surface engageable with the inner shaft for rotation therewith.

10. A surgical instrument as recited in claim 7, wherein the engagement element includes an inner surface engageable with the inner shaft for rotation therewith.

11. A surgical instrument as recited in claim 1, wherein the screw has an outer thread surface connectable with a mating surface of the receiver.

12. A surgical instrument as recited in claim 1, wherein the drive is integrally connected with a sleeve of the first member.

13. A spinal implant system comprising:

a surgical instrument including an outer tubular sleeve extending between a proximal end and a distal end including a drive engageable with a bone fastener shaft, and an inner shaft being rotatable relative to the sleeve and including a screw connectable with a threaded surface of a bone fastener receiver;

an implant support including extender tabs configured for engagement with the bone fastener receiver;

a guide member including an inner surface that defines a cavity configured for disposal of the sleeve and an image guide being oriented relative to a sensor to communicate a signal representative of a position of the guide member; and a tracking device including a sensor that receives the signal and communicates with a processor to generate data for display of an image from a monitor, the image representing position of the guide member relative to tissue.

14. A spinal implant system as recited in claim 13, wherein the guide member includes an end effector of a robotic arm.

15. A spinal implant system as recited in claim 13, wherein the drive is integrally connected with the sleeve.

16. A spinal implant system as recited in claim 13, wherein each extender tab includes proximal spring tips engageable with a pocket surface of the sleeve.

17. A spinal implant system as recited in claim 13, wherein the screw is axially translatable relative to the inner shaft between a non-locking configuration and a locking configuration with the threaded surface of the bone fastener receiver.

18. A spinal implant system comprising:

a surgical instrument including an outer tubular sleeve extending between a proximal end and a distal end including a drive engageable with a bone fastener shaft, and an inner shaft being rotatable relative to the sleeve and including a screw connectable with a threaded surface of a bone fastener receiver;

an implant support including extender tabs configured for engagement with the bone fastener receiver; and a guide member including an inner surface that defines a cavity configured for disposal of the sleeve and an image guide being oriented relative to a sensor to communicate a signal representative of a position of the guide member, wherein each extender tab includes proximal spring tips engageable with a pocket surface of the sleeve.

19. A spinal implant system as recited in claim 18, wherein the guide member includes an end effector of a robotic arm.

* * * * *